(12) United States Patent
Janardhanan et al.

(10) Patent No.: US 10,371,528 B2
(45) Date of Patent: Aug. 6, 2019

(54) PEDESTRIAN NAVIGATION DEVICES AND METHODS

(71) Applicant: TEXAS INSTRUMENTS INCORPORATED, Dallas, TX (US)

(72) Inventors: Jayawardan Janardhanan, Bellevue, WA (US); Jaiganesh Balakrishnan, Bangalore (IN)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 998 days.

(21) Appl. No.: 14/323,823

(22) Filed: Jul. 3, 2014

(65) Prior Publication Data
US 2016/0003622 A1 Jan. 7, 2016

(51) Int. Cl.
*G01C 21/12* (2006.01)
*G01C 22/00* (2006.01)
(Continued)

(52) U.S. Cl.
CPC .............. *G01C 21/12* (2013.01); *A61B 5/112* (2013.01); *G01C 22/006* (2013.01);
(Continued)

(58) Field of Classification Search
CPC ...... G01C 21/12; G01C 22/006; G01C 21/16; A61B 5/112; A61B 2562/0219; G01P 15/18
(Continued)

(56) References Cited

U.S. PATENT DOCUMENTS

2009/0254294 A1   8/2009  Dutta
2010/0004860 A1*  1/2010  Chernoguz .......... G01C 22/006
                                              701/494
(Continued)

FOREIGN PATENT DOCUMENTS

CN   103727959 A   4/2014
EP      1253404   10/2002
RU       134633   11/2013

OTHER PUBLICATIONS

European Search Report dated Jun. 27, 2018.

*Primary Examiner* — Alexander Satanovsky
(74) *Attorney, Agent, or Firm* — Kenneth Liu; Charles A. Brill; Frank D. Cimino

(57) ABSTRACT

Devices and methods for pedestrian navigation are disclosed. In an embodiment, a device includes an accelerometer sensor configured to sense acceleration components associated with a device motion in a plurality of axes of the accelerometer sensor. The acceleration components include stride frequency components and step frequency components. The device includes a processing module communicably associated with the accelerometer sensor. The processing module is configured to process at least a portion of the acceleration components to determine an estimated attitude associated with the device motion with respect to the accelerometer sensor. The processing module is configured to filter out the step frequency components by blocking the stride frequency components. The processing module is further configured to determine the estimated attitude based on the step frequency components to thereby mitigate a bias in the estimated attitude associated with a lateral sway of the device motion.

12 Claims, 6 Drawing Sheets

(51) Int. Cl.
*G01C 21/16* (2006.01)
*A61B 5/11* (2006.01)
*G01P 15/18* (2013.01)

(52) U.S. Cl.
CPC ...... *A61B 2562/0219* (2013.01); *G01C 21/16* (2013.01); *G01P 15/18* (2013.01)

(58) Field of Classification Search
USPC ......... 702/104, 141, 150, 160, 189; 701/494
See application file for complete search history.

(56) References Cited

U.S. PATENT DOCUMENTS

| | | | |
|---|---|---|---|
| 2010/0174506 A1* | 7/2010 | Joseph | G01C 21/165 |
| | | | 702/141 |
| 2012/0086606 A1* | 4/2012 | Mathews | G01C 21/165 |
| | | | 342/461 |
| 2012/0136573 A1* | 5/2012 | Janardhanan | G01C 21/165 |
| | | | 701/512 |
| 2012/0296221 A1* | 11/2012 | Morren | A61B 5/113 |
| | | | 600/484 |
| 2013/0311134 A1* | 11/2013 | Kordari | G06F 17/10 |
| | | | 702/160 |
| 2014/0129178 A1* | 5/2014 | Meduna | G06F 17/00 |
| | | | 702/189 |

* cited by examiner

PEDESTRIAN NAVIGATION DEVICES AND METHODS

TECHNICAL FIELD

The present disclosure relates to pedestrian navigation.

BACKGROUND

Pedestrian navigation devices are used to determine user location information on streets. A number of such navigations devices can also be in the form of unstrapped devices that can be held by their users in random patterns. Such navigation devices determine a user direction of motion by estimating an attitude associated with the user direction. The attitude can be defined, for example, as a direction of a user motion (or device motion as the navigation device is carried by the user) with respect to a sensor direction, wherein the sensor direction is known to the navigation device. In some scenarios, attitude estimation can be performed in a static manner; however, this methodology can involve the user pointing the navigation device in the direction of user motion, whereby the attitude in this direction is defined by a quantified value of "zero". That being said, it is noted that dynamic estimation of the attitude can help to reduce or preclude restrictions on an orientation of the navigation device; for example, a user can be able to change the orientation of a navigation device from portrait to landscape, or even carry the navigation device in his or her shirt or trouser pockets and subsequently take the navigation device out in order to view a map associated with pedestrian navigation. Dynamic attitude estimation in unstrapped pedestrian navigation using low-cost sensors (for example, accelerometers, electronic compasses (e-compasses), gyroscopes, etc.) for navigation devices (which can be, for example, embodied in mobile devices) is an industry-wide problem.

SUMMARY

This Summary is provided to introduce a selection of concepts in a simplified form that are further described below in the Detailed Description. This Summary is not intended to identify key or essential features of the claimed subject matter, nor is it intended to be used as an aid in determining the scope of the claimed subject matter.

A number of devices and methods for pedestrian navigation are disclosed. In an embodiment, a device includes an accelerometer sensor configured to sense acceleration components associated with a device motion in a plurality of axes of the accelerometer sensor. The acceleration components include stride frequency components and step frequency components. The device includes a processing module communicably associated with the accelerometer sensor. The processing module is configured to process at least a portion of the acceleration components to determine an estimated attitude associated with the device motion with respect to the accelerometer sensor. The processing module is configured to process the acceleration components by filtering out the step frequency components of the acceleration components by blocking the stride frequency components of the acceleration components. The processing module is further configured to determine the estimated attitude based on the step frequency components of the acceleration components to thereby mitigate a bias in the estimated attitude associated with a lateral sway of the device motion.

In some embodiments, a method operable in a device for pedestrian navigation includes determining a direction of an accelerometer sensor of the device with respect to a global reference direction, sensing acceleration components associated with a device motion in a plurality of axes of the accelerometer sensor. The acceleration components include stride frequency components and step frequency components. The method further includes electronically processing the acceleration components to determine an estimated attitude of the device motion with respect to the accelerometer sensor. The electronically processing at least includes filtering out the step frequency components of the acceleration components by blocking the stride frequency components of the acceleration components, and determining the estimated attitude based on the step frequency components of the acceleration components to thereby mitigate a bias in the estimated attitude associated with a lateral sway of the device motion. The method further includes electronically combining the estimated attitude with the direction of the accelerometer sensor to generate a user heading estimation.

In some embodiments, a method operable in a device for pedestrian navigation includes sensing acceleration components associated with a device motion in a plurality of axes of an accelerometer sensor. The acceleration components include stride frequency components and step frequency components. The method further includes electronically processing at least a portion of the acceleration components to determine an estimated attitude of the device motion with respect to the accelerometer sensor. The electronically processing at least includes filtering out the step frequency components of the acceleration components by blocking the stride frequency components of the acceleration components, and determining the estimated attitude based on the step frequency components of the acceleration components to thereby mitigate a bias in the estimated attitude associated with a lateral sway of the device motion.

DETAILED DESCRIPTION

Various embodiments for attitude estimation in pedestrian navigation devices are described in reference to FIGS. 1 to 7.

"Pedestrian navigation" as used herein includes any one, some or all of position, direction, heading, tilt, attitude, azimuth, altitude, velocity, acceleration and jerk sensing and/or location-based applications, position-based applications, pedometer applications, map-related applications, trajectory control, course monitoring and completion, restriction to confined areas or zones, manoeuvring, free fall detection, image acquisition control, image stabilization, and other applications combining or benefiting from any of the foregoing.

Various devices that are capable of providing attitude estimation, or more specifically that are capable of providing pedestrian navigation, are portable devices, hand-held devices, or mobile devices. Such devices can include any electronic devices, such as those stated herein as well as others, that are sufficiently movable in position or orientation to utilize and benefit from the embodiments and teachings herein, and such devices are hereinafter referred to as 'pedestrian navigation devices".

It should be noted that a pedestrian navigation device is configured to calculate a speed and/or distance estimation of the user carrying the pedestrian navigation device, a direction of one or more sensors present in the pedestrian navigation device with respect to a pre-specified direction (e.g. magnetic north), and an estimated attitude delivering direction of such mobile device with respect to a direction of device motion (or the user motion such as walking direction) with respect to an accelerometer sensor. In some example embodiments, the pedestrian navigation device may only be configured to calculate the direction of one or more sensors present in the pedestrian navigation device with respect to the pre-specified direction and the estimated attitude associated with the pedestrian navigation device. In such example embodiments, the speed and/or distance estimation can be performed by a suitable device (for example, a pedometer) that is accessible to, or in communication with the pedestrian navigation device (also referred to as 'device') disclosed herein for the attitude estimation. Alternatively, in some example embodiments, a device such as the pedometer may also be embodied in the pedestrian navigation device.

Figure 1:
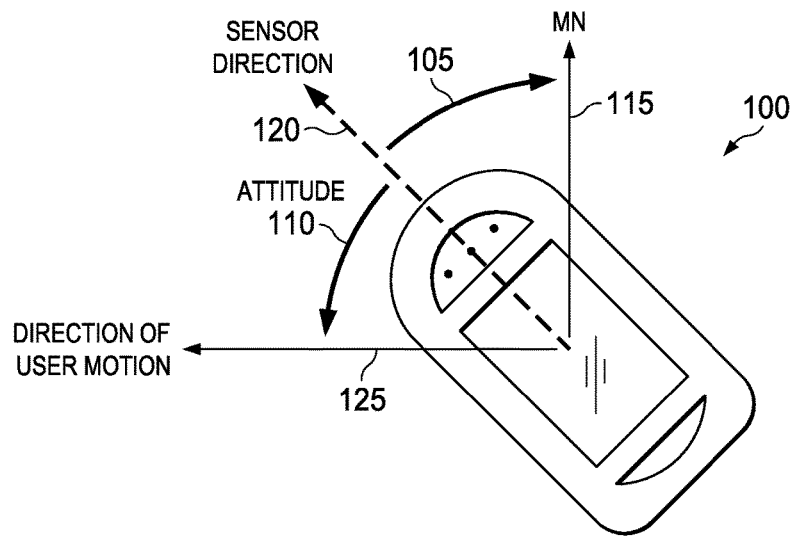
FIG. 1 is an example representation of a device positioned to illustrate attitude and sensor direction with respect to a global reference direction, in accordance with an embodiment.

Referring to FIG. 1, an example representation of a device 100 (a pedestrian navigation device) is shown. The device 100 is configured to be used with both unstrapped and strapped navigation devices, and can be carried by a user to determine a user heading direction (user heading estimation). Herein, for the purposes of the description, the unstrapped navigation is split into estimating distance travelled by the user and the user heading estimation separately. The distance travelled by the user is estimated using pedometer process and circuitry embodiments as known in the art. Various embodiments of the present technology provide solutions for the user heading estimation.

In various embodiments, the user heading estimation is performed by determining two estimations, where a first estimation is a direction of a device sensor (for example, an accelerometer sensor) with respect to a global reference direction (for example, North), and a second estimation is a direction (attitude) of the user motion (also referred to as 'device motion', as the user carries the device 100) with respect to the device sensor. The first estimation is determined using an e-compass and/or a gyroscope, and the second estimation (attitude) is determined by a processing module along with the accelerometer sensor. In an example embodiment, the device 100 can only determine an estimated attitude, and the direction of the device sensor with respect to the global reference direction can be provided by another device, and both the estimated attitude and the direction of the device sensor are combined to determine the user heading estimation. Various embodiments of the accelerometer sensor and the processing module are herein described with reference to FIGS. 2 to 7.

As shown in FIG. 1, the device 100 is configured to determine the user heading estimation by determining two directions, an angle 105 and an angle 110. The angle 105 represents a direction difference between a Magnetic North (see, MN 115) and a sensor direction (120), and the angle 110 represents a direction difference between the sensor direction 120 and a direction of user or device motion (see, 125). For the purposes of the description, if the device 100 is placed in a horizontal plane, the direction 110 is herein referred to as "attitude" associated with the device motion (or the user motion).

Figure 2:
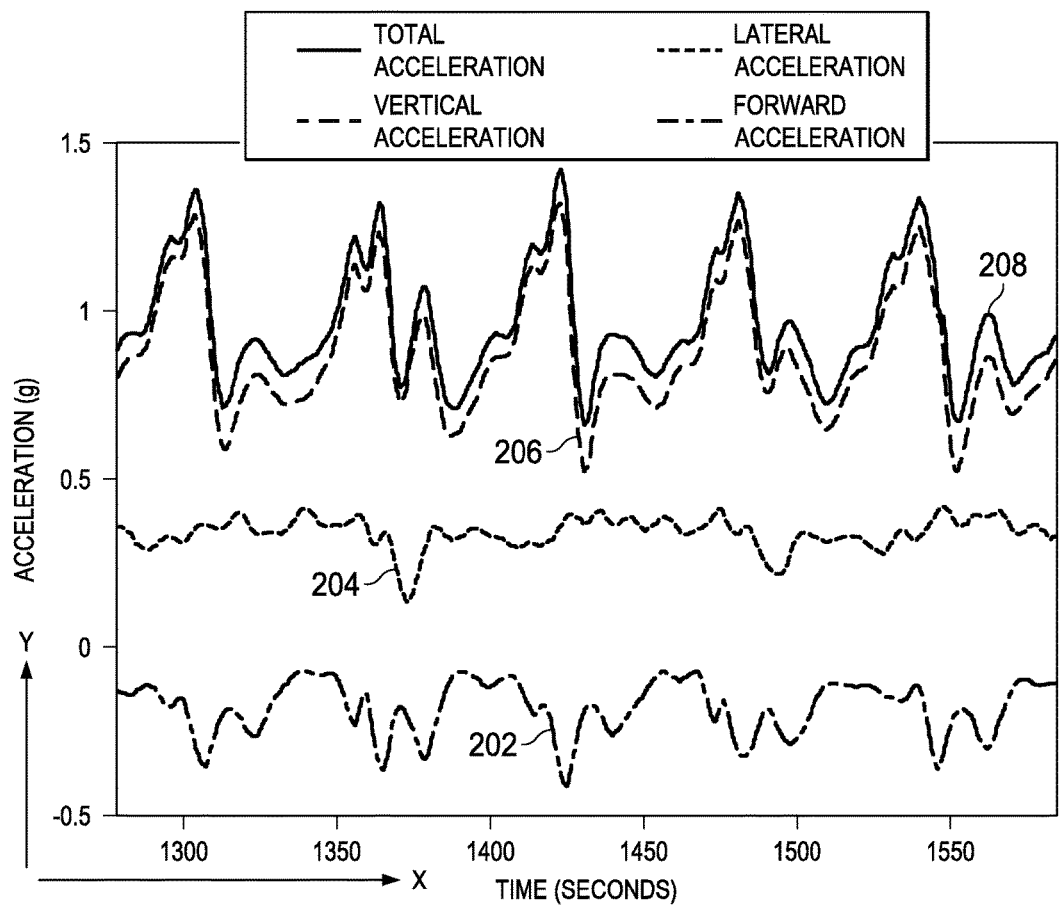
FIG. 2 is a graph illustrating example waveforms of acceleration components measurements versus time for each of three accelerometer axes and an overall acceleration component.

In FIG. 2, raw accelerometer measurements (acceleration components) versus time are shown. The acceleration components during a typical user walking motion (or the device motion as the device is carried by the user) such as a forward component (shown as a forward acceleration 202) of a user, a lateral component (shown as a lateral acceleration 204) of the user and a vertical component (shown as a vertical acceleration 206) of the user are shown in FIG. 2.

In FIG. 2, a magnitude (Amag), for example, a square root of sum of squared values of the acceleration components (a forward acceleration 202, a lateral acceleration 204 and a vertical acceleration 206) is also graphed at top of the graph (shown as total acceleration 208). These accelerations are plotted on a vertical axis (Y-axis) with respect to time on the horizontal axis (X-axis). From the plots of FIG. 2, it should be noted that a variance of the vertical acceleration 206 is a maximum and a variance along the lateral acceleration 204 is a minimum, among the forward acceleration 202, the lateral acceleration 204 and the vertical acceleration 206. Furthermore, the vertical acceleration 206 and the forward acceleration 202 are offset in phase by about 90 degree or nearly a quarter of step duration. For instance, as waveform of the vertical acceleration 206 leads a waveform of the forward acceleration 202 by approximately 90 degrees as shown in FIG. 2.

Figure 3:
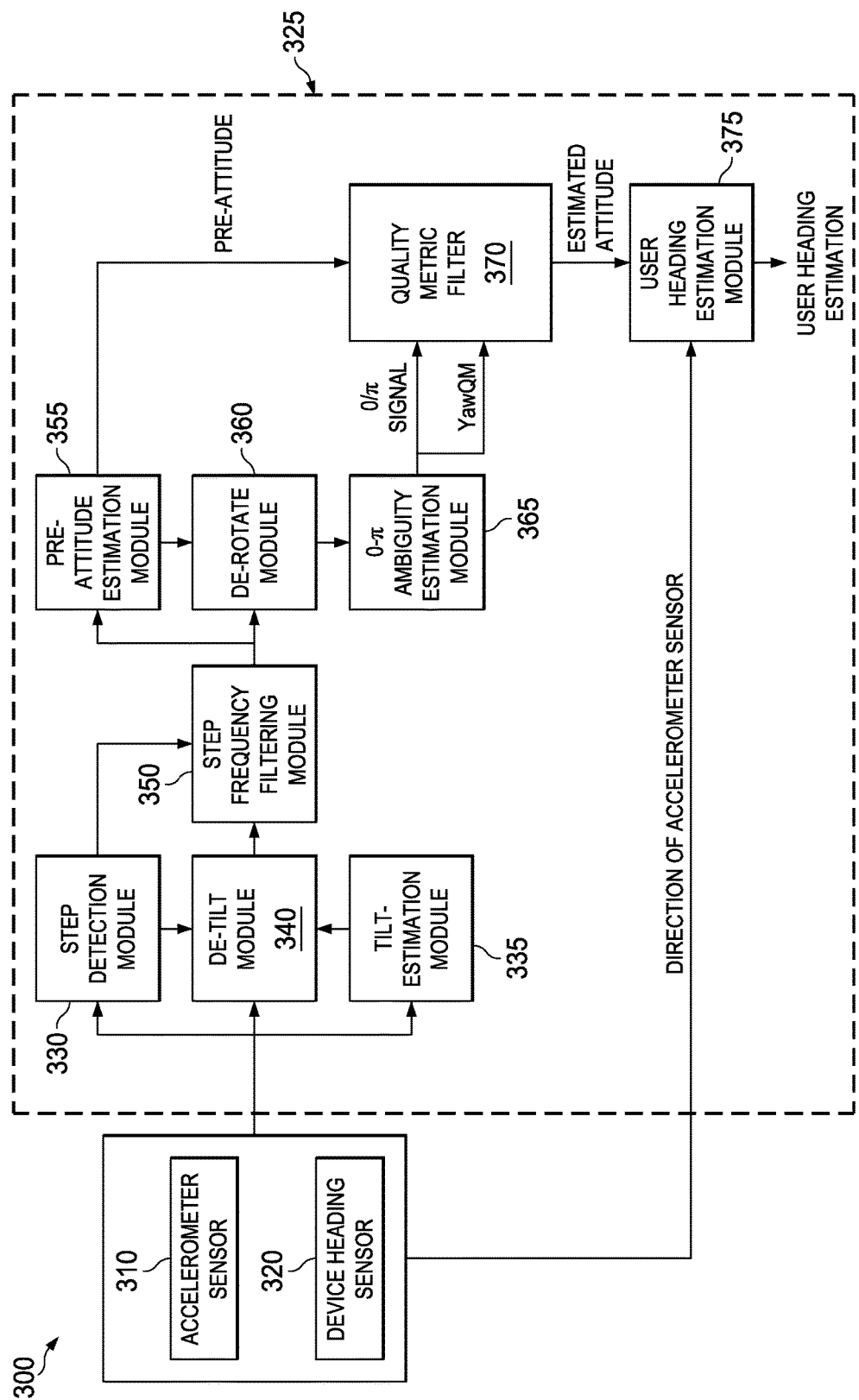
FIG. 3 illustrates an example block diagram representation of a device for pedestrian navigation, in accordance with an example embodiment.

FIG. 3 illustrates a block diagram of a device 300 for pedestrian navigation, in accordance with an example embodiment of the present technology. The device 300 is an example of the device 100. The device 300 includes an accelerometer sensor 310 and a processing module 325. The accelerometer sensor 310 is configured to sense acceleration components associated with a device motion in a plurality of axes of the accelerometer sensor 310. In an example embodiment, the device 300 also includes a device heading sensor 320 that is physically situated in a fixed relationship to the accelerometer sensor 310 and is configured to generate a device heading estimation with respect to a global reference direction (such as a global North). The processing module 325 is configured to determine an estimated attitude associated with the device motion with respect to the accelerometer sensor 310, and is further configured to determine a user heading estimation based on combining the estimated attitude and the device heading estimation.

In an example embodiment, the accelerometer sensor 310 is a three-axis accelerometer and provides measurements of the acceleration components, for example, AccX, AccY, AccZ, along three axes X, Y and Z, respectively, of the accelerometer sensor 310. Without loss of generality, it should be noted that the accelerometer sensor 310 is an imaginary observer inside the device 300 (an example of the device 100) and blind to the outside. If a plane (X-axis) of the device 300 coincides with the horizontal plane, the AccX is an acceleration component in a direction emanating outwardly from a display of the device 300 along the plane of the device 300, the AccY is an acceleration component in a lateral direction, for example, in Y-axis that is perpendicular to the direction of X-axis in the horizontal plane, and the AccZ is an acceleration component in a vertical plane, for example perpendicular from the display of the device 300. It can be visualized that the accelerometer sensor 310 is an imaginary observer inside the device 300 and is blind to the outside, so that the X-axis always points to top of the device 300 irrespective of the orientation of the device 300, and the angular relation between the AccX, AccY, AccZ remain constant irrespective of the orientation of the device 300, and these axes are not necessarily same as the axes of personal navigation coordinates. Examples of the device heading sensor 320 can include, but are not limited to, a gyroscope and an encompass that provides information of the direction of the accelerometer sensor 310 with respect the a global reference direction, for example, magnetic North.

The processing module 325 can include a variety of devices knows to those skilled in the art to facilitate or enable the execution or performance of software instructions, protocols, or logical instructions stored on a data storage device or received therein. The processing module 325 can be embodied as a multi-core processor, a single core processor, or a combination of multi-core processors and single core processors. For example, the processing module 325 can be embodied as one or more of various processing means such as a co-processor, a microprocessor, a controller, a digital signal processor (DSP), processing circuitry with or without an accompanying DSP, or various other processing devices including integrated circuits such as, for example, an application specific integrated circuit (ASIC), a field programmable gate array (FPGA), a microcontroller unit (MCU), a hardware accelerator, a special-purpose computer chip, or the like. The processing module 325 can also include memory devices (for example, a processor cache), time keeping devices (for example, a real-time clock (RTC)), and/or additional circuitry or data transmission channels. The data storage device can also be embodied by a number of different devices or combination of devices. For instance, the data storage device can include one or more volatile and/or non-volatile memory devices. Examples of such devices include, but are not limited to, dynamic random access memory (DRAM), static random access memory (SRAM), programmable read-only memory (PROM), erasable programmable read-only memory (EPROM), and electrically erasable programmable read-only memory (EEPROM).

The processing module 325 includes a step detection module 330, a tilt-estimation module 335, a de-tilt module 340 and a step frequency filtering module 350.

The step detection module 330 is configured to determine step frequency components and stride frequency components in the accelerometer components (AccX, AccY and AccZ). In an example embodiment, the step detection module 330 determines these frequency components using information of zero crossings in the acceleration measurements and assumption that the step Frequency is equal to 2/Stride Period. However, the step detection module 330 can determine the step frequency components and the stride frequency components based on pattern detection and estimation in the accelerometer components (AccX, AccY and AccZ). The tilt-estimation module 335 is configured to determine tilt measurements, for example, pitch ($\Phi$) and roll ($\theta$) outputs using the acceleration components (AccX, AccY, AccZ) received from the accelerometer sensor 310 and the information of the step frequency components and the stride frequency components (received from the step detection module 330). In some embodiments, the tilt measurements can usually be estimated during a rest period of the user motion by averaging the samples during the rest period to filter noise, as during user motion, the measurements are likely too noisy to average for tilt estimation. In some example embodiments, whenever a stride is detected, the tilt-estimation module 335 is configured to average measurements over the stride for the dynamic tilt estimation (and tracking), as the acceleration measurement waveforms are in general periodic across the stride and a net acceleration is usually zero (except for a vertical acceleration component).

The de-tilt module 340 is configured to process the acceleration components to generate de-tilted acceleration components along a plurality of personal navigation axes based on the tilt measurements. In an example embodiment, the plurality of personal navigation axes includes at least a vertical axis, a first horizontal axis and a second horizontal axis. For instance, de-tilting is changing the accelerometer components AccX, AccY, AccZ into accelerometer components in the first horizontal axis, the second horizontal axis and the vertical axis, respectively. For example, the tilt-estimation module 335 determines an existing orientation of the device 300 and then de-tilts to determine accelerometer readings in the vertical axis and in a horizontal 2-D plane. In an example embodiment, the tilt-estimation module 335 provides the tilt measurements (the pitch ($\Phi$) and the roll ($\theta$) outputs) corresponding to AccX, AccY, AccZ to the de-tilt module 340. The de-tilt module 340 in turn utilizes all of these inputs (AccX, AccY, AccZ, $\Phi$ and $\theta$) to determine de-tilted axes of a pedestrian personal coordinate system (X', Y', V'). In the description following herein, references will be made to de-tilted coordinates (X', Y', V'), which are coordinates (axes) a personal coordinate system of the pedestrian, where coordinate X' corresponds to the first horizontal axis, Y' to the second horizontal axis, and V' to the vertical axis.

In so much, in various use scenarios, significant sideways sway of a user depending on nature of walk of the user gives rise (deviation) to the lateral acceleration component (shown by 204 in FIG. 2) in the accelerometer measurements. Such unwanted deviation in the lateral acceleration component 204 can otherwise bias the estimation of attitude (determination of the estimated attitude). As such, the sideways sway is periodic with stride frequency (half of the step frequency), where a stride is made of two consecutive steps (for example, a left step and a right step). In an example embodiment, the step frequency filtering module 350 is configured to generate filtered acceleration components by blocking stride frequency components from the de-tilted acceleration components. For example, the step frequency filtering module 350 is configured to filter the stride frequency components and to pass only the step frequency components of the de-tilted acceleration components. The processing module 325 is configured to determine the estimated attitude associated with the device motion based on processing of the step frequency components of the de-tilted acceleration components. As such, the estimated attitude is interlinked with other measurements and estimates, any filtering which introduces group delay would complicate the estimation of the attitude. Without loss of generality, an example of the step frequency filtering module 350 is a Fast Fourier transform (FFT) based block filter. If a stride (2 steps) is already detected, by passing one stride worth data through the ITT based block filter, the transform components would be F(0) (a DC component), F(1) (a stride frequency) and F(2) (a step frequency). The FFT based block filter is configured to block the F(1) and pass only the component F(2) (the step frequency component) for further processing for the estimation of the attitude. In other example embodiments, the step frequency components can also be computed using Goertzel algorithm or any other suitable means.

For the purposes of the description, the filtered acceleration components are referred to as a first horizontal acceleration component (AccX') along the first horizontal axis, a second horizontal acceleration component (AccY') along the second horizontal axis, and a vertical acceleration component (AccV) along the vertical axis. The filtered acceleration components (AccX', AccY' and AccV) are subsequently processed to determine the estimated attitude associated with the device motion. For instance, the output (AccX', AccY' and AccV) of the step frequency filtering module 350 is provided to a pre-attitude estimation module 355 and a de-rotate module 360. In an example embodiment, the pre-attitude estimation module 355 provides a pre-attitude estimation output as an input to the de-rotate module 360. The pre-attitude estimation module 355 operates to calculate a pre-attitude based on an assumption that a variance of acceleration is minimum along the lateral direction of the device motion, and is maximum along the vertical axis AccV. Further, in the horizontal plane, it is assumed that the variance is maximum along the forward direction and minimum along the lateral direction of the device motion. Accordingly, the pre-attitude estimation module 355 is configured to calculate the pre-attitude by finding an axis of maximum variance (an estimate of the forward direction) in the horizontal plane of the personal navigation coordinates, based on the values of the AccX' and AccY'. It should be noted that the pre-attitude only provides a pre-estimation of the forward direction of the device motion with respect to the accelerometer direction, though it still has a 0-π ambiguity (as whether the direction of the device motion is in a forward direction or in a backward direction).

Without loss of generality, in an example embodiment, the pre-attitude can be determined by the pre-attitude estimation module 355 based on the following equation:

$$\text{pre-attitude} = \frac{1}{2}\tan^{-1}\left(\frac{-2R_{xy}}{R_{xx} - R_{yy}}\right) \quad \text{eq. (1)}$$

where $R_{xx}$ is auto-covariance of AccX', $R_{yy}$ is auto-covariance of AccY', and $R_{xy}$ is cross-covariance of AccX' and AccY'. Herein, the AccX' and AccY' represent the filtered acceleration components in the first horizontal axis and the second horizontal axis (of the personal navigation axes) that are received from the step frequency filtering module 350.

In an example embodiment, the de-rotate module 360 is configured to generate a pre-forward acceleration component, for example AccF' (in the axis of maximum variance in the horizontal plane) based on the AccX', AccY' and the pre-attitude. For instance, by rotating the AccX' and AccY' by an angle corresponding to the pre-attitude, the pre-forward acceleration component AccF' (acceleration in the direction of the maximum variance in the horizontal plane) can be pre-estimated. In an example embodiment, the de-rotate module 360 is also configured to provide a pre-lateral acceleration component (for example, AccL') based on the AccX', AccY' and the pre-attitude. For instance, by rotating the AccX', AccY' by the angle corresponding to the pre-attitude, the pre-lateral acceleration component (AccL') can be pre-estimated. It should be noted that the pre-attitude only provides a pre-estimation of the forward direction of the device motion with respect to the accelerometer sensor direction, though it still has a 0-π ambiguity (as to whether the direction of device motion is in the forward direction or the backward direction).

In an example embodiment, a 0-π ambiguity estimation module 365 is configured to resolve the 0-π ambiguity of the input received from the de-rotate module 360 (that is obtained on the basis of estimated pre-attitude). In an example embodiment, the 0-π ambiguity estimation module 365 is configured to detect a sense of a leading relation or a lagging relation between the pre-forward acceleration component (AccF') and the vertical acceleration component (AccV) based on a cross-covariance of the pre-forward acceleration component (AccF') and the vertical acceleration component (AccV) that is phase rotated by 90 degree. In this example embodiment, the 0-π ambiguity estimation module 365 is configured to determine whether the direction of the device motion is the forward direction or the backward direction, based on the detected sense of a relation (the leading relation or the lagging relation between the AccF' and AccV).

In an example embodiment, the 0-π ambiguity estimation module 365 determines the estimated attitude based on the following equation:

estimated attitude=pre-attitude+π, if $R_{fv}$<0; and estimated attitude=pre-attitude, if $R_{fv}$>0      eq. (2)

where $R_{fv}$ is a cross-covariance of AccF' and AccV phase rotated by 90° (90 degree) equivalently delayed by quarter step duration. From the equation (2), it should be noted that an estimated user direction is the forward direction if the cross-covariance ($R_{fv}$) between the AccF' and the AccV phase rotated by 90° is positive, and where the estimated user direction is the backward direction if the cross-covariance ($R_{fv}$) between the AccF' and the AccV phase rotated by 90° is negative. Accordingly, in an example embodiment, a forward acceleration of the device motion (represented by AccF) is calculated based on the pre-forward acceleration component AccF' and detected sense of relation between the AccF' and AccV. Similarly, a lateral acceleration of the device motion (represented by AccL) is calculated based on the pre-lateral acceleration component AccL' and detected sense of relation between the AccF' and AccV.

In another example embodiment, a processing module such as the processing module 325 does not include the 0-π ambiguity estimation module 365, and the processing module can be configured to determine the attitude based on the following equation:

attitude=$\tan^{-1}(R_{xv}/R_{yv})$+π/2,      eq. (3)

where $R_{xv}$ is a cross-covariance of AccX' with AccV, and $R_{yv}$ is a cross-covariance of AccY' with AccV.

In an example embodiment, the processing module 325 is configured to refine the estimated attitude obtained by equations (2) or (3) to provide a high-quality stream of attitude estimations. For instance, the 0-π ambiguity estimation module 365 is configured to provide a quality metric factor (YawQM) for the attitude estimation based on the following equation:

$$YawQM = \frac{R_{fv}}{\sqrt{R_{ff}R_{vv}}} \quad \text{eq. (4)}$$

where is a cross-covariance of the AccF (forward acceleration component) and the AccV (vertical acceleration component), $R_{ff}$ and $R_{vv}$ are auto-covariances of the AccF and the AccV, respectively. It should be noted that if the value of YawQM is close to ±1, the attitude estimation is accurate. If the value of YawQM is close to zero, even small levels of 'noise' can result in a sign inversion giving rise to erroneous estimation of the attitude. Accordingly, based on the magnitude of YawQM, the estimated attitude is further refined to generate a refined estimated attitude (also referred to as a 'quality filtered attitude' or also the 'estimated attitude').

In an example embodiment, the processing module 325 includes a quality metric filter 370 that is configured to determine the refined estimated attitude (also referred to as the 'estimated attitude') based on the pre-attitude (received from the pre-attitude estimation module 355), a sense of the lagging relation or the leading relation between AccF' and AccV (received from the 0-π ambiguity estimation module 365), and the YawQM. In an example embodiment, the processing module 325 includes a user heading estimation module 375 that receives the inputs, namely the device heading estimation (received from the device heading sensor 320) and the estimated attitude (received from the quality metric filter 370). The user heading estimation module 375 is configured to electronically combine the estimated attitude with the device heading estimation to generate a user heading estimation that provides the user heading direction with respect to the global reference direction (for example, North). In an example embodiment, the device 300 does not include the quality metric filter 370, and the 0-π ambiguity estimation module 365 resolves the 0-π ambiguity of the input received from the de-rotate module 360 and provides the estimated attitude. In this embodiment, the user heading estimation module 375 can combine the estimated attitude (received from the 0-π ambiguity estimation module 365) with the device heading estimation to generate the user heading estimation.

Figure 4:
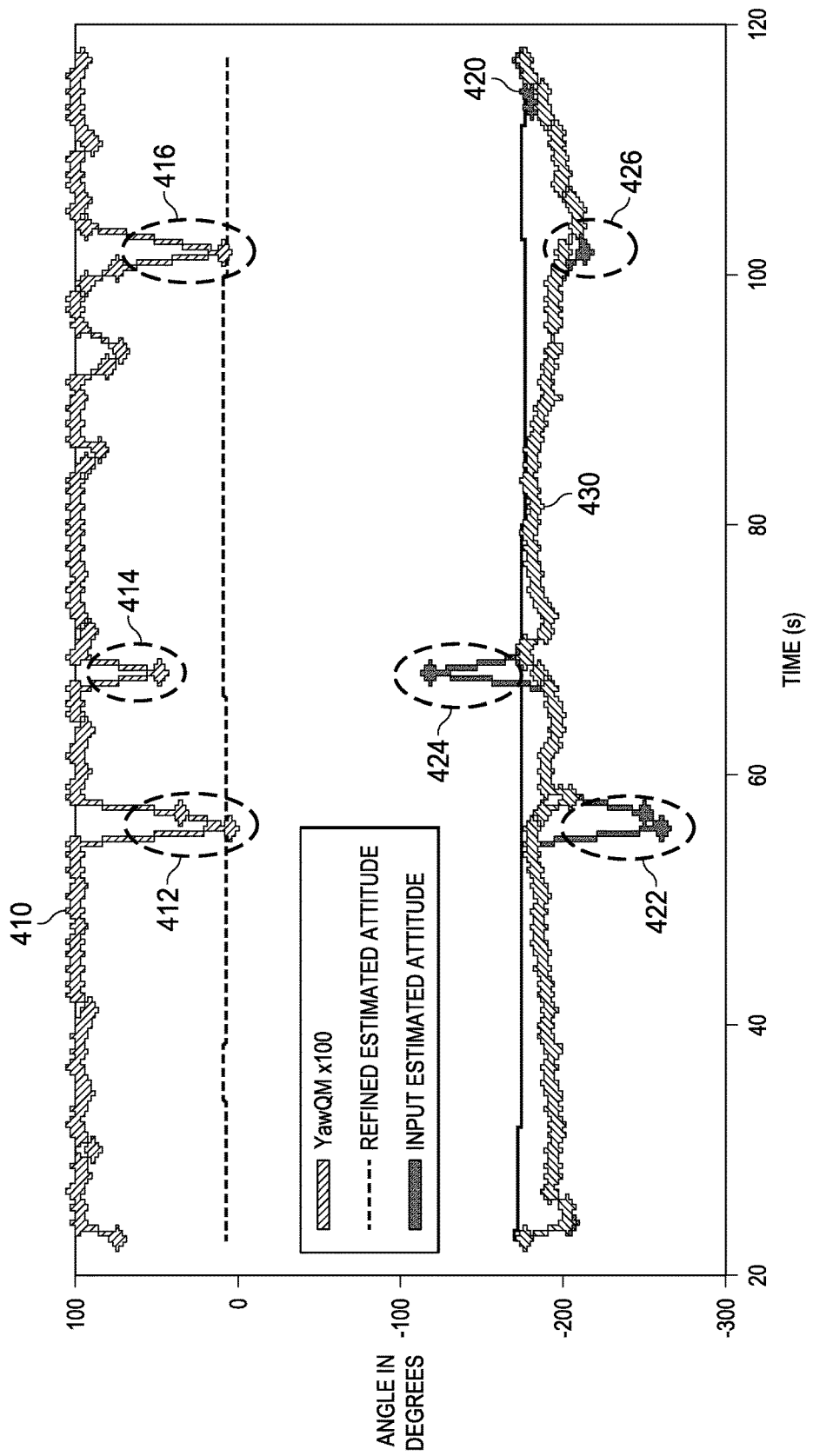
FIG. 4 is a graph illustrating example plots associated with quality metric filtering of attitude estimation, in accordance with an embodiment.

An example representation of plots associated with the quality metric filtering is shown in FIG. 4. Referring to FIG. 4, a graph of magnitude (angle) of estimated attitude (for example, determined from equation (2)), YawQM (determined from equation (4)), and refined estimated attitude (or quality filtered attitude) with respect to time are shown. For instance, a plot 410 represents the YawQM, a plot 420 represents the input estimated attitude (obtained from pre-attitude estimation module 355 and the 0-π ambiguity estimation module 365) and a plot 430 represents the refined estimated attitude.

It should be noted that in FIG. 4, the refined estimated attitude (shown by 430) is a filtered estimated attitude that is obtained based on filtering the input estimated attitude (shown by 420) based on the magnitude of the YawQM (shown by 410). For instance, a portion 422 (corresponding to a portion 412), a portion 424 (corresponding to a portion 414) and a portion 426 (corresponding to a portion 416) of the input estimated attitude (shown by 420) are blocked in the refined estimated attitude (shown by 430).

Figure 5A:
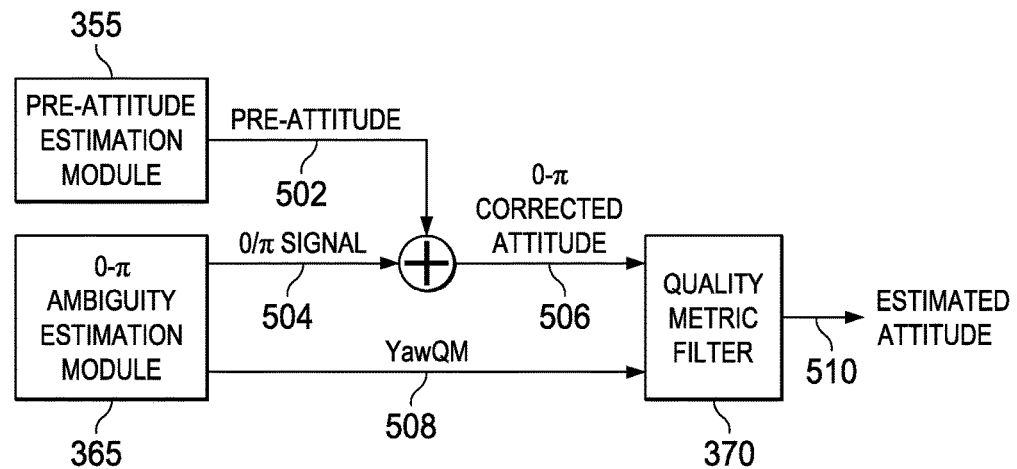
FIG. 5A illustrates an example block diagram representation of quality metric filtering, in accordance with an embodiment.
Figure 5B:
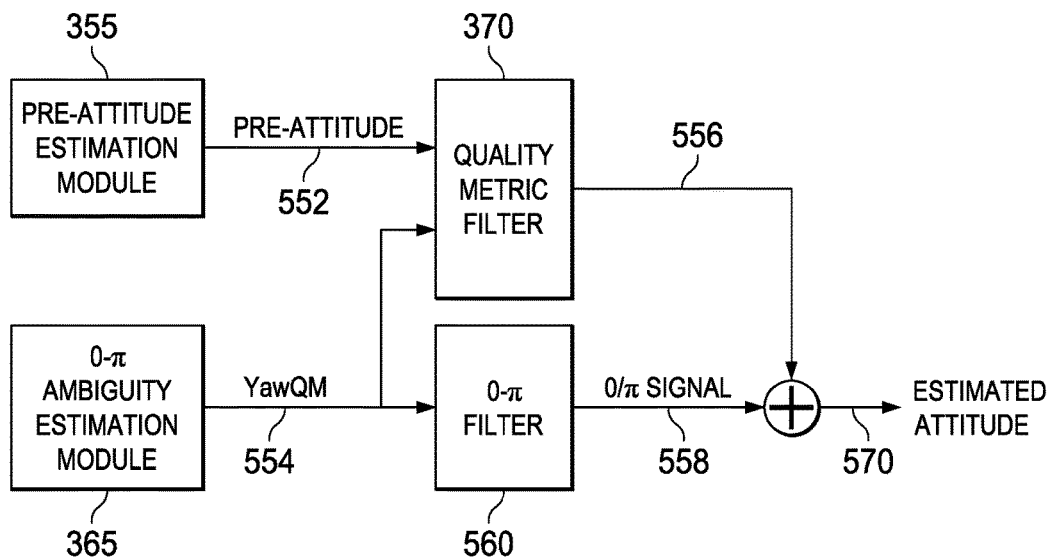
FIG. 5B illustrates an example block diagram representation of quality metric filtering, in accordance with another embodiment.

Some example embodiments of implementations of quality metric filtering to generate the refined estimated attitude are shown in FIGS. 5A and 5B. As shown in FIG. 5A, the pre-attitude (see, 502) received by the pre-attitude estimation module 355 is corrected by a 0/π signal (or input) (see, 504 that represent a leading/lagging relation between AccF' and AccV) received by the 0-π ambiguity estimation module 365 to generate a 0-π corrected attitude (see, 506). Further, the quality metric filter 370 receives the 0-π corrected attitude 506 and YawQM (see, 508) as inputs and is configured to generate the estimated attitude (see, 510) that is a refined estimated attitude.

In this example embodiment of FIG. 5A, the quality metric filter 370 can generate the refined estimated attitude Yaw based on the following equation:

$$YawFilt_n = Yaw_n * abs(YawQM) + YawFilt_{n-1} * (1-abs(YawQM)) \quad \text{eq. (5),}$$

where $YawFilt_n$ is an estimated attitude at a time $t_n$, $YawFilt_{n-1}$ is an estimated attitude at a time $t_{n-1}$, and $Yaw_n$ is an attitude estimated based on the pre-attitude and the direction of the device motion at the time $t_n$. From the above equation (5), it should be noted that as the YawQM approaches zero, the $YawFilt_n$ is nearly equal to the preceding refined estimated attitude, for example, equal to $YawFilt_{n-1}$. Further, as the YawQM approaches one, the $YawFilt_n$ is equal to a current value of the estimated attitude, for example $Yaw_n$.

Another embodiment of determining the refined estimated attitude is shown in FIG. 5B. As shown in FIG. 5B, the pre-attitude (see, 552) is filtered based on the YawQM (see, 554, received from the 0-π ambiguity estimation module 365) by a quality metric filter 370 to generate a filtered attitude signal (see, 556). In this embodiment, the pre-attitude 552 is filtered based on a saturated value of the YawQM, for example, the filtered attitude signal (see, 556) is generated when the YawQM is substantially equal to one.

In this embodiment, a signal representing 0-π (see, 0/π signal 558) is generated by a separate 0-π filter 560, and the refined estimated attitude (570) is generated based on the filtered attitude signal 556 and the signal 558.

It should be noted that some of the features described in this specification have been presented as modules (for example, the tilt-estimation module 335, the pre-attitude estimation module 355, etc), in order to more particularly emphasize their implementation independence. A module can be implemented as a hardware circuit including custom very large scale integration (VLSI) circuits or gate arrays, off-the-shelf semiconductors such as logic chips, transistors, or other discrete components. A module can also be implemented in programmable hardware devices such as field programmable gate arrays, programmable array logic, programmable logic devices, graphics processing units, and the like.

A module described herein can also be at least partially implemented in software for execution by various types of processors. An identified unit of executable code can, for instance, include one or more physical or logical blocks of computer instructions which can, for instance, be organized as an object, procedure, or function. Nevertheless, the executables of an identified module need not be physically located together, but can include disparate instructions stored in different locations which, when joined logically together, include the module and achieve the stated purpose for the module. Further, modules can be stored on a computer-readable medium, which can be, for instance, a hard disk drive, flash device, random access memory (RAM), tape, or any other such medium used to store data.

Indeed, a module of executable code could be a single instruction, or many instructions, and can even be distributed over several different code segments, among different programs, and across several memory devices. Similarly, operational data can be identified and illustrated herein within modules, and can be embodied in any suitable form and organized within any suitable type of data structure. The operational data can be collected as a single data set, or can be distributed over different locations including over different storage devices, and can exist, at least partially, merely as electronic signals on a system or network.

Various example embodiments of methods of attitude estimation and determination of user heading estimation are implicitly described with reference to FIGS. 3 to 5B. Some example embodiments of the methods/processes are further provided with reference to FIGS. 6 and 7.

Figure 6:
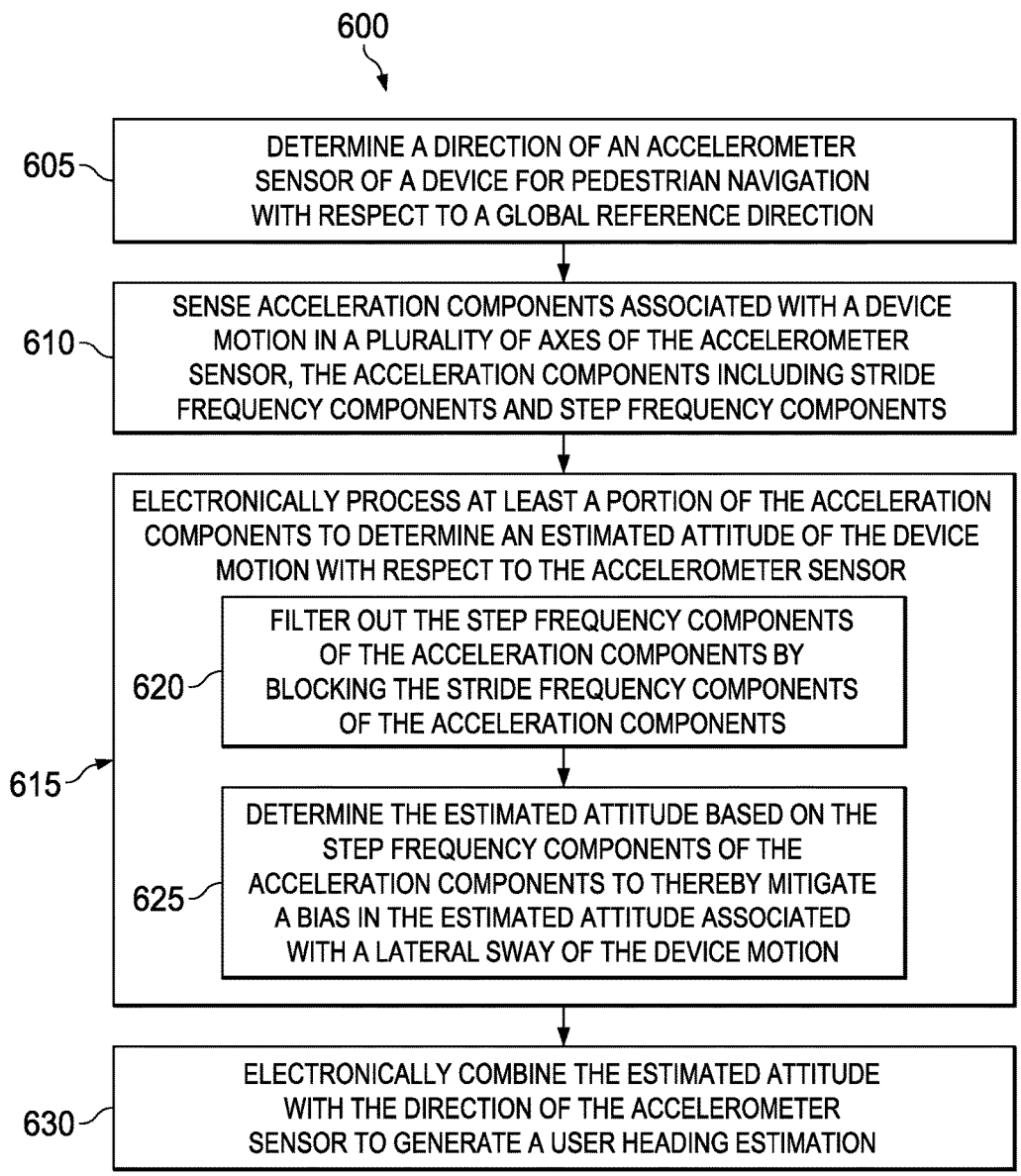
FIG. 6 illustrates a flow diagram of an example method of pedestrian navigation, in accordance with an embodiment.

Referring now to FIG. 6, a method 600 is illustrated, in accordance with an embodiment of the present technology. The method 600 can be implemented in navigation devices, for example devices 100 or 300 as described with reference to FIGS. 1 and 3.

At 605, the method 600 includes determining a direction of an accelerometer sensor of a device for pedestrian navigation with respect to a global reference direction. For the purposes of the description a direction of an accelerometer sensor of the device with respect to a global reference direction is also referred to as a 'device heading direction'. For instance, the device heading direction is a direction of a device sensor (for example, the accelerometer sensor 310) with respect to the global reference direction, for example magnetic North. The device heading direction can be determined by suitable device heading sensors including, but not limited to, a gyroscope and an e-compass that provide information of the direction of the accelerometer sensor with respect the global reference direction.

At 610, the method 600 includes sensing acceleration components associated with a device motion in a plurality of axes of the accelerometer sensor. In an example embodiment, the accelerometer sensor such as the accelerometer sensor 310 (for example, a three-axis accelerometer) provides measurements of the acceleration components in three axes. The accelerometer components are with respect to a plane of the device, and their direction of measurements is fixed irrespective of the orientation of the device. In an example, measurement of the acceleration components can be along three axes X, Y and Z, for example, AccX, AccY, and AccZ respectively as described with reference to FIG. 3. Without loss of generality, the AccX is an acceleration component in an outward direction emanating from a display of the device in the plane of the device, the AccY is an acceleration component in a lateral direction emanating in the plane of the device perpendicular to the AccX, and AccZ is an acceleration component emanating beyond the display in the plane of the device and perpendicular to the AccX and AccY. For instance, if the device is placed in a horizontal plane, the AccX and AccY are acceleration measurements in the horizontal plane and the AccZ is an acceleration measurement in the vertical plane.

At 615, the method 600 includes electronically processing at least a portion of the acceleration components to determine an estimated attitude associated with the device motion with respect to the accelerometer sensor. The operation of block 615 includes at least two operations performed by blocks 620 and 625. At 620, the method 600 includes filtering out step frequency components of the acceleration components by blocking stride frequency components of the acceleration components. Further, at 625, the method 600 includes determining the estimated attitude associated with the device motion based on the step frequency components of the acceleration components, thereby mitigating a bias in the estimated attitude associated with a lateral sway of the device motion.

At 630, the method 600 includes electronically combining the estimated attitude with the direction of the accelerometer sensor of the device with respect to the global reference direction (determined at 605) to generate a user heading estimation.

In an example embodiment, the operations of the blocks 605 and 630 can be optional and the method 600 can only include the operations of the blocks 610 and 615 (including 620 and 625) for determining the estimated attitude. It should be noted that certain operations provided in FIG. 6 are described herein as constituting distinct steps performed in a certain order. Such implementations are examples only and non-limiting in scope. Certain operation can be grouped together and performed in a single operation, and certain operations can be performed in an order that differs from the order employed in the examples set forth herein. For instance, the operation of determining a device heading estimation (shown at 605) can be performed along with the operation performed at block 630 or at an immediately preceding operation of the operation performed at the block 630. Moreover, certain operations of the methods 600 are performed in an automated fashion. These operations involve substantially no interaction with the user. Other operations of the methods 600 can be performed in a manual or a semi-automatic fashion. These operations involve interaction with the user via one or more user interface presentations.

Figure 7:
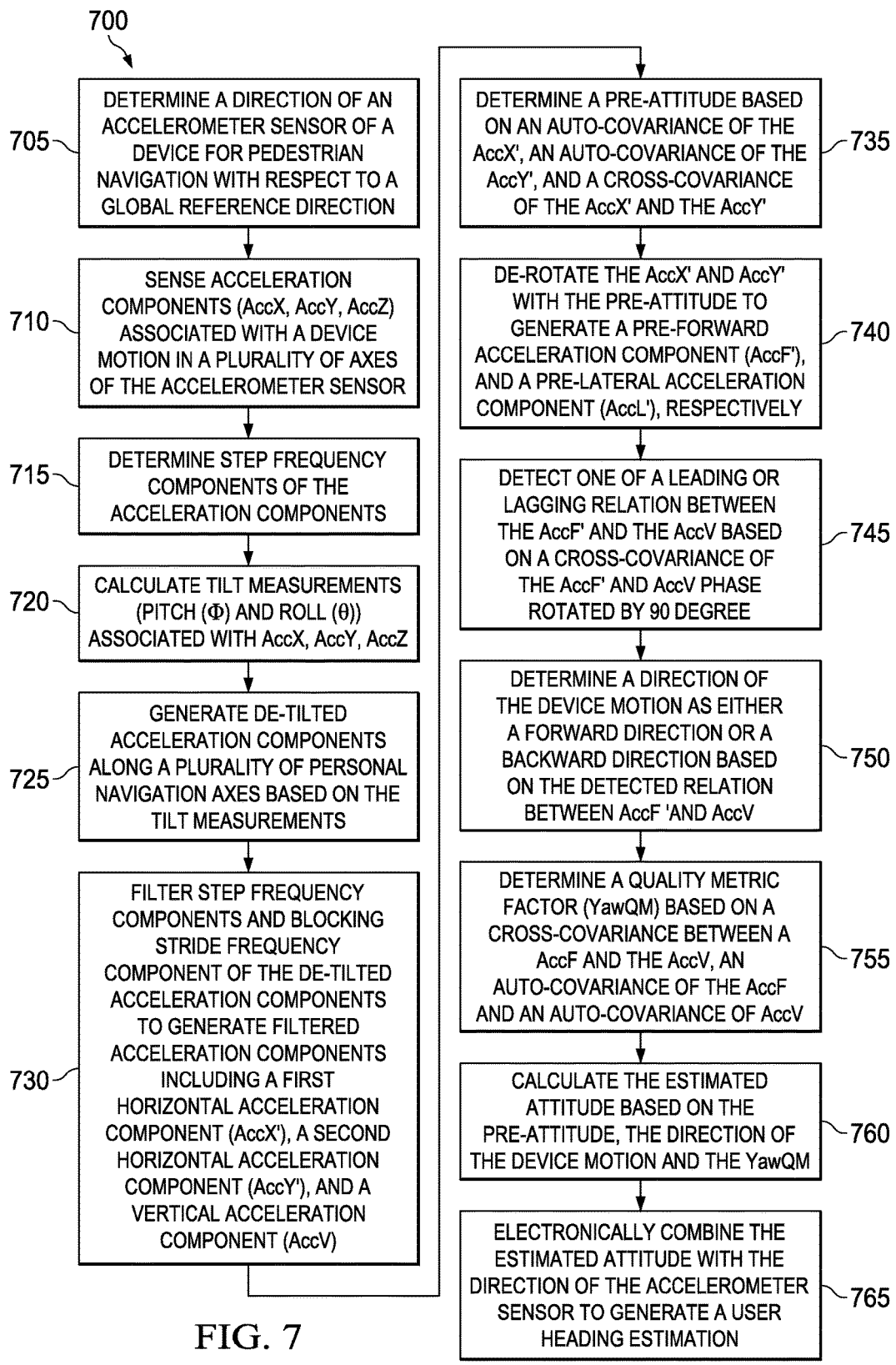
FIG. 7 illustrates a flow diagram of an example method of pedestrian navigation, in accordance with another embodiment.

Referring now to FIG. 7, an example embodiment of a method 700 for the attitude estimation and thereafter user heading estimation is shown. At 705, the method 700 includes determining a direction of an accelerometer sensor of a device with respect to a global reference direction. An example of the operation 705 is the operation 605 described with reference to FIG. 6.

At 710, the method 700 includes sensing acceleration components associated with a device motion in a plurality of axes (also referred to as 'user motion', as the user carries the device). An example of the operation 710 is the operation 610 described with reference to FIG. 6. Examples of the acceleration components are AccX, AccY, and AccZ as described with reference to FIG. 3.

At 715, the method 700 includes determining step frequency components of the acceleration components. At 720, the method 700 includes calculating tilt measurements (for example, pitch ($\Phi D$) and roll ($\theta$)) associated with the acceleration components (AccX, AccY, and AccZ respectively). At 725, the method 700 includes generating de-tilted acceleration components along a plurality of personal navigation axes based on the tilt measurements. In an example embodiment, the plurality of personal navigation axes includes at least a vertical axis, a first horizontal axis and a second horizontal axis.

At 730, the method 700 includes filtering the de-tilted acceleration components to retain only the step frequency components by blocking stride frequency components of the de-tilted acceleration components to generate filtered acceleration components. For the purposes of this description, the filtered acceleration components includes three measurements that are termed as a first horizontal acceleration component (AccX'), a second horizontal acceleration component (AccY'), and a vertical acceleration component (AccV).

At 735, the method 700 includes determining a pre-attitude based on the equation:

$$\text{pre-attitude} = \frac{1}{2}\tan^{-1}\left(\frac{-2R_{xy}}{R_{xx} - R_{yy}}\right)$$

where $R_{xx}$ is an auto-covariance of the first horizontal acceleration component, $R_{yy}$ is an auto-covariance of the second horizontal acceleration component, and $R_{xy}$ is a cross-covariance of the first horizontal acceleration component and the second horizontal acceleration component. The pre-attitude provides a direction of maximum variance in the horizontal plane.

At 740, the method 700 includes de-rotating the first horizontal acceleration component (AccX') in response to the pre-attitude to generate a pre-forward acceleration component (AccF'). For instance, by rotating the AccX' by an angle corresponding to the pre-attitude, the pre-forward acceleration component (acceleration in the direction of the maximum variance in the horizontal plane) can be pre-estimated. In an example embodiment, at 740, the method 700 also includes de-rotating the second horizontal acceleration component (AccY') in response to the pre-attitude to generate a pre-lateral acceleration component (AccL').

At 745, the method 700 includes detecting one of a leading relation or a lagging relation between the pre-forward acceleration component (AccF') and the vertical acceleration component (AccV) based on, a cross-covariance of the AccF' and the vertical acceleration component AccV that is phase rotated by 90 degree. For instance, a relation (either the leading relation or the lagging relation between the AccF' and the AccV) is determined based on a cross-covariance of the AccF' and AccV phase rotated by 90 degree. At 750, the method 700 includes determining a direction of the device motion as either a forward direction or a backward direction based on the detected relation between the AccF' and the AccV. The determined direction of the device motion represents whether the device motion is in forward direction or in the backward direction. In an example embodiment, by determining the direction of the device motion, a 0-π ambiguity is resolved.

In an example embodiment, the method 700 can include an operation for determining the estimated attitude associated with the device motion based on the pre-attitude and the direction of the device motion. In some other example embodiments, the method 700 further refines the estimated attitude by a quality metric filtering for getting rid of infrequent 90°/180° error in estimating the attitude caused by spurious turns in user motion.

In an example embodiment, at step 755, the method 700 optionally includes refining the estimated attitude obtained by equations (2) and (3) to provide a high-quality stream of attitude estimations. For instance, a quality metric factor is determined based on the equation:

$$YawQM = \frac{R_{fv}}{\sqrt{R_{ff}R_{vv}}}$$

where $R_{fv}$ is a cross-covariance of AccF (forward acceleration component) and AccV (vertical acceleration component), $R_{ff}$ and $R_{vv}$ are auto-covariances of the AccF and AccV, respectively. It should be noted that if the value of YawQM is close to ±1, the attitude estimation is better. If the value of YawQM is close to zero, even small levels of 'noise' can result in a sign inversion giving rise to erroneous estimation of the attitude. Accordingly, based on the magnitude of YawQM, the estimated attitude is further refined to generate a refined estimated attitude (also referred to as a 'quality filtered attitude' or also the 'estimated attitude').

At block 760, the method 700 includes calculating estimated attitude based on the pre-attitude (determined at block 735), the direction of the device motion (determined at block 750) and the YawQM (determined at block 755).

At block 765, the method 700 includes electronically combining the estimated attitude with the direction of the accelerometer sensor with respect to the global reference direction (determined at block 705) to generate a user heading estimation. The user heading estimation provides a user heading direction with respect to the global reference direction, for example North.

It should be noted that certain operations provided in FIG. 7 are described herein as constituting distinct steps performed in a certain order. Such implementations are examples only and non-limiting in scope. Certain operation can be grouped together and performed in a single operation, and certain operations can be performed in an order that differs from the order employed in the examples set forth herein. For instance, the operation of determining the direction of the accelerometer sensor (shown at 705) can be performed along with the operation performed at block 765 or as an immediately preceding operation to the operation performed at the block 765. Moreover, certain operations of the methods 700 are performed in an automated fashion. These operations involve substantially no interaction with the user. Other operations of the methods 700 can be performed in a manual or a semi-automatic fashion. These operations involve interaction with the user via one or more user interface presentations.

Without in any way limiting the scope, interpretation, or application of the claims appearing below, effects of one or more of the example embodiments disclosed herein is to provide attitude estimation that precludes erroneous measurements caused by the lateral sway associated with the device motion (or the user motion). Various embodiments of the present technology provide closed form estimation of attitude, for example, the estimation of the attitude is performed on the basis of set mathematical expressions that provide accurate attitude estimation and are computationally effective. Further, the estimated attitude is refined by a quality metric filtering that gets rid of the infrequent 90°/180° in determining the user heading direction. As the computation of the quality metric is performed for each instantaneous estimate of the attitude, filtering of the estimated attitude across time with quality metric offers more accuracy to the attitude estimation. Furthermore, various embodiments of the present technology offer cost effective and effective solutions for pedestrian navigation by using low cost micro-electromechanical systems (MEMS) sensor which can be integrated in mobile applications like a cellphone. It should be noted that reference throughout this specification to features, advantages, or similar language does not imply that all of the features and advantages should be or are in any single embodiment. Rather, language referring to the features and advantages is understood to mean that a specific feature, advantage, or characteristic described in connection with an embodiment is included in at least one embodiment of the present technology. Thus, discussions of the features and advantages, and similar language, throughout this specification but do not necessarily, refer to the same embodiment.

Various embodiments of the present disclosure, as discussed above, are practiced with steps and/or operations in a different order, and/or with hardware elements in configurations which are different than those which are disclosed. Therefore, although the technology has been described based upon these example embodiments, it is noted that certain modifications, variations, and alternative constructions are apparent and well within the spirit and scope of the technology.

Although the present technology has been described with reference to specific exemplary embodiments, it is noted that various modifications and changes is made to these embodiments without departing from the broad spirit and scope of the present technology. For example, the various devices, modules, analyzers, generators, etc., described herein is enabled and operated using hardware circuitry (e.g., a complementary metal oxide semiconductor (CMOS) based logic circuitry), and/or any combination of hardware and software (e.g., embodied in a machine readable medium). For example, the various electrical structures may be embodied using transistors, logic gates, and electrical circuits (e.g., ASIC circuitry and/or in Digital Signal Processor (DSP) circuitry) and drawings are to be regarded in an illustrative rather than a restrictive sense.

Although various example embodiments of the present technology are described herein in a language specific to structural features and/or methodological acts, the subject matter defined in the appended claims is not necessarily limited to the specific features or acts described above. Rather, the specific features and acts described above are disclosed as example forms of implementing the claims.

What is claimed is:

1. A pedestrian navigation device comprising:
   an accelerometer sensor to sense acceleration components associated with a device motion of the device in a plurality of axes of the accelerometer sensor, wherein the acceleration components include stride frequency components and step frequency components; and
   a processing module coupled to the accelerometer sensor determine an estimated attitude associated with the device motion by:
      determining tilt measurements associated with the acceleration components;
      generating de-tilted acceleration components along each of a vertical axis, a first horizontal axis, and a second horizontal axis based on the tilt measurements;
      filtering the de-tilted acceleration components to remove data corresponding to the stride frequency components to produce filtered acceleration components, wherein the filtered acceleration components include a vertical acceleration component along the vertical axis, a first horizontal acceleration component along the first horizontal axis, and a second horizontal acceleration component along the second horizontal axis;
      determining a pre-attitude based on an auto-covariance of the first horizontal acceleration component ($R_{xx}$), an auto-covariance of the second horizontal acceleration component ($R_{yy}$), and a cross-covariance of the first horizontal acceleration component and the second horizontal acceleration component ($R_{xy}$);
      determining a quality metric factor based on a cross-covariance between a forward acceleration component and the vertical acceleration component ($R_{fv}$), an auto-covariance of the forward acceleration component ($R_{ff}$), and an auto-covariance of the vertical acceleration component ($R_{vv}$);
      determining the estimated attitude based on the quality metric factor, the pre-attitude, and a direction of the device motion; and
      determining a user heading estimation based on the estimated attitude.

2. The pedestrian navigation device of claim 1, comprising a device-heading sensor arranged in a fixed relationship to the accelerometer sensor and configured to determine a direction of the accelerometer sensor with respect to a global reference direction, wherein the determination of the user heading estimation by the processing module is made by combining the estimated attitude with the direction of the accelerometer sensor.

3. The pedestrian navigation device of claim 1, wherein the pre-attitude is determined as:

$$\text{pre-attitude} = \frac{1}{2}\tan^{-1}\left(\frac{-2R_{xy}}{R_{xx} - R_{yy}}\right).$$

4. The pedestrian navigation device of claim 1, wherein the estimated attitude is determined as:

YawFilt$_n$=Yaw$_n$*abs(YawQM)+YawFilt$_{n-1}$*(1−abs(YawQM));

wherein YawFilt$_n$ is the estimated attitude at a time $t_n$, YawFilt$_{n-1}$ an estimated attitude at a time $t_{n-1}$, YawQM is the quality metric factor, and Yaw$_n$ is an attitude determined based on the pre-attitude and the direction of the device motion at the time $t_n$.

5. The pedestrian navigation device of claim 1, wherein the quality metric factor is determined as:

$$YawQM = \frac{R_{fv}}{\sqrt{R_{ff}R_{vv}}}.$$

6. A pedestrian navigation device comprising:
   an accelerometer sensor to sense acceleration components associated with a device motion of the device in a plurality of axes of the accelerometer sensor, wherein the acceleration components include stride frequency components and step frequency components; and
   a processing module coupled to the accelerometer sensor determine an estimated attitude associated with the device motion by:
      determining tilt measurements associated with the acceleration components;
      generating de-tilted acceleration components along each of a vertical axis, a first horizontal axis, and a second horizontal axis based on the tilt measurements;
      filtering the de-tilted acceleration components to remove data corresponding to the stride frequency components to produce filtered acceleration components, wherein the filtered acceleration components include a vertical acceleration component along the vertical axis, a first horizontal acceleration component along the first horizontal axis, and a second horizontal acceleration component along the second horizontal axis;
      determining a pre-attitude based on an auto-covariance of the first horizontal acceleration component ($R_{xx}$), an auto-covariance of the second horizontal acceleration component ($R_{yy}$), and a cross-covariance of the first horizontal acceleration component and the second horizontal acceleration component ($R_{xy}$);

determining a direction of the device motion;

determining a quality metric factor based on a cross-covariance between an acceleration component corresponding to the direction of the device motion and the vertical acceleration component, an auto-covariance of the acceleration component corresponding to the direction of the device motion, and an auto-covariance of the vertical acceleration component;

determining the estimated attitude based on the quality metric factor, the pre-attitude, and the direction of the device motion; and determining a user heading estimation based on the estimated attitude.

7. The pedestrian navigation device of claim 6, wherein the direction of the device motion is determined to be either a forward direction of a backward direction.

8. The pedestrian navigation device of claim 7, wherein the processing module is configured to de-rotate the first horizontal acceleration component in response to the pre-attitude to generate a pre-forward acceleration component.

9. The pedestrian navigation device of claim 8, wherein the direction of the device motion is determined as the forward direction or the backward direction by determining whether the pre-forward acceleration and the vertical acceleration component have a leading relation the vertical acceleration component rotated by a 90 degree phase.

10. The pedestrian navigation device of claim 9, wherein:

the direction of the device motion is the forward direction if a cross-covariance between the pre-forward acceleration component and the 90 degree phase rotated vertical acceleration component is positive; and the direction of the device motion is the backward direction if the cross-covariance between the pre-forward acceleration component and the 90 degree phase rotated vertical acceleration component is negative.

11. The pedestrian navigation device of claim 8, wherein the processing module is configured to de-rotate the second horizontal acceleration component in response to the pre-attitude to generate a pre-lateral acceleration component.

12. The pedestrian navigation device of claim 11, wherein the pre-attitude is determined as:

$$\text{pre-attitude} = \tan^{-1}(R_{xv}/R_{yv}) + \pi/2;$$

where $R_{xv}$ is a cross-covariance of the pre-forward acceleration component and the vertical acceleration component and $R_{yv}$ is a cross-covariance of the pre-lateral acceleration component and the vertical acceleration component.

* * * * *